(12) United States Patent
Lehman

(10) Patent No.: US 8,960,195 B2
(45) Date of Patent: *Feb. 24, 2015

(54) INTUBATION-FACILITATING OXYGEN MASK

(71) Applicant: Edward Lehman, Las Vegas, NV (US)

(72) Inventor: Edward Lehman, Las Vegas, NV (US)

( * ) Notice: Subject to any disclaimer, the term of this patent is extended or adjusted under 35 U.S.C. 154(b) by 33 days.

This patent is subject to a terminal disclaimer.

(21) Appl. No.: 13/758,852

(22) Filed: Feb. 4, 2013

(65) Prior Publication Data

US 2013/0172768 A1    Jul. 4, 2013

Related U.S. Application Data

(63) Continuation of application No. 12/764,313, filed on Apr. 21, 2010, now Pat. No. 8,365,734.

(60) Provisional application No. 61/173,816, filed on Apr. 29, 2009.

(51) Int. Cl.
*A61M 16/06* (2006.01)
*A61M 16/08* (2006.01)
(Continued)

(52) U.S. Cl.
CPC ............ *A61M 16/06* (2013.01); *A61M 16/085* (2014.02); *A61M 16/125* (2014.02); *A61B 5/082* (2013.01);
(Continued)

(58) Field of Classification Search
USPC ............ 128/200.11, 200.14, 200.23, 200.24, 128/200.26, 201.17, 201.23, 201.25, 128/201.26, 202.27, 203.12, 203.15, 128/203.29, 205.19, 205.25, 205.27, 128/205.29, 206.11, 206.12, 206.21, 128/206.24, 206.28, 206.29, 207.14, 207.18
See application file for complete search history.

(56) References Cited

U.S. PATENT DOCUMENTS

| 4,328,797 A | 5/1982 | Rollins, III et al. |
| D351,226 S | 10/1994 | Parvatharaj |

(Continued)

FOREIGN PATENT DOCUMENTS

GB    2332375    6/1999

OTHER PUBLICATIONS

"How to Improve Oxygenation and Patient Safety and Reduce Stresses and Healthcare Costs by Transforming an Ineffective Nasal Cannula to a Technically Simple and Effective Face Tent in 10 seconds," http://tsemask.com/.

(Continued)

*Primary Examiner* — Annette Dixon
(74) *Attorney, Agent, or Firm* — H. John Rizvi; Gold & Rizvi P.A.

(57) ABSTRACT

A versatile, intubation-facilitating oxygen mask is provided including at least one diaphragm configured with a continuous, flexible, modifiable membrane from which an instrument-access port may be manually constructed, when and if needed. The novel oxygen mask preferably includes a multiple-inlet port having a standard oxygen tube connector and an interchangeable breathing-therapy device connector, a carbon dioxide sampling port, an exhaust port, and a nose clip. The mask can be worn as a standard oxygen mask during traditional oxygen therapy, yet quickly converted into an intubation mask. The clinician manually perforates the nasal and/or oral membranes of the one or more diaphragms to create a point and size of entry perfectly matched to the requirements for a variety of procedures that may be performed involving nasally or orally introduced scopes or probes—without disturbing the ongoing benefits of increased oxygen saturation and continuous monitoring of expired gases.

18 Claims, 6 Drawing Sheets

(51) Int. Cl.
*A61M 16/12* (2006.01)
*A61B 5/08* (2006.01)
*A61B 5/097* (2006.01)
*A61B 7/02* (2006.01)
*A61M 16/00* (2006.01)
*A61M 16/04* (2006.01)
*A61M 16/16* (2006.01)
*A61B 1/267* (2006.01)
*A61B 1/273* (2006.01)
*A61M 11/00* (2006.01)
*A61B 1/01* (2006.01)

(52) U.S. Cl.
CPC ............... *A61B 5/097* (2013.01); *A61B 7/023* (2013.01); *A61M 16/0078* (2013.01); *A61M 16/0461* (2013.01); *A61M 16/0875* (2013.01); *A61M 16/12* (2013.01); *A61M 16/16* (2013.01); *A61B 1/2676* (2013.01); *A61B 1/2736* (2013.01); *A61M 16/0463* (2013.01); *A61M 16/0683* (2013.01); *A61M 2202/0208* (2013.01); *A61M 2230/432* (2013.01); *A61M 11/00* (2013.01); *A61B 1/01* (2013.01)
USPC ............ 128/206.28; 128/206.21; 128/205.25

(56) References Cited

U.S. PATENT DOCUMENTS

| | | |
|---|---|---|
| 5,400,781 A | 3/1995 | Davenport |
| 5,431,158 A * | 7/1995 | Tirotta ................ 128/206.21 |
| 5,465,712 A | 11/1995 | Malis et al. |
| 5,474,060 A * | 12/1995 | Evans ................... 128/204.22 |
| 5,533,708 A * | 7/1996 | Atkinson et al. ......... 251/149.1 |
| 5,586,551 A | 12/1996 | Hilliard |
| 5,694,929 A | 12/1997 | Christopher |
| 5,701,886 A | 12/1997 | Ryatt |
| 2,332,375 A | 6/1999 | Broome |
| 6,386,198 B1 | 5/2002 | Rugless |
| 6,792,943 B2 | 9/2004 | Kumar et al. |
| 7,669,595 B1 * | 3/2010 | Mitchell ................ 128/203.12 |
| 8,365,734 B1 * | 2/2013 | Lehman ................. 128/206.28 |
| 2003/0024533 A1 * | 2/2003 | Sniadach ................ 128/205.25 |
| 2006/0081248 A1 | 4/2006 | McDonald |
| 2008/0053449 A1 | 3/2008 | Lindblom et al. |

OTHER PUBLICATIONS

Metropolitan Medical Online Products. Patil-Syracuse Type Clear Silicone Masks. http://www.metropolitanmedical.com/prod/PatTypCle_01.htm.

"No Cost TSE 'Mask': A New Type of Oxygen Face Tent for Sedation, Monitored Anesthesia Care and Total IV Anesthesia." http://www.tsemask.com/.

VBM Anesthesia Intensive Care Product Catalog. Dec. 2007. p. 12.

\* cited by examiner

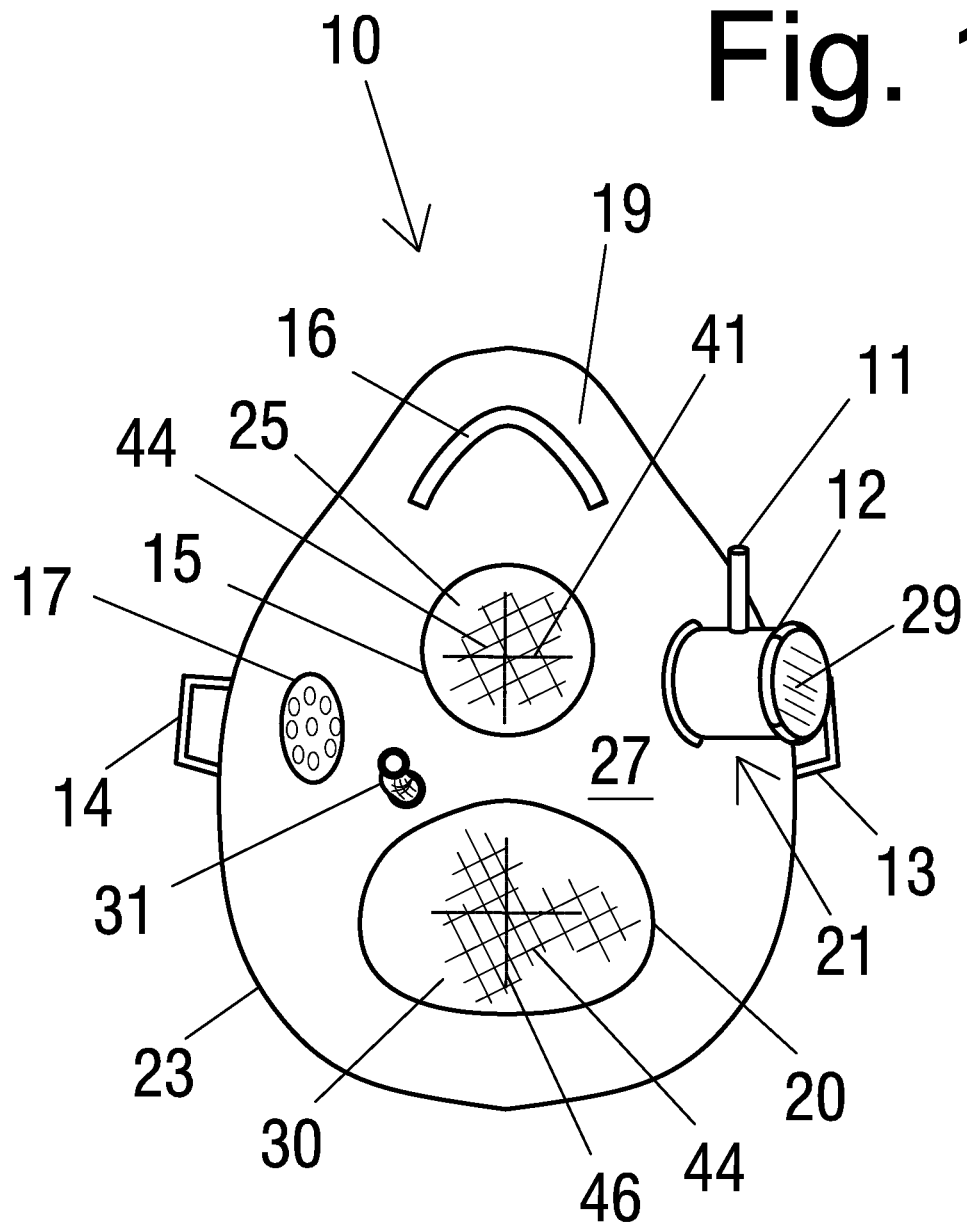

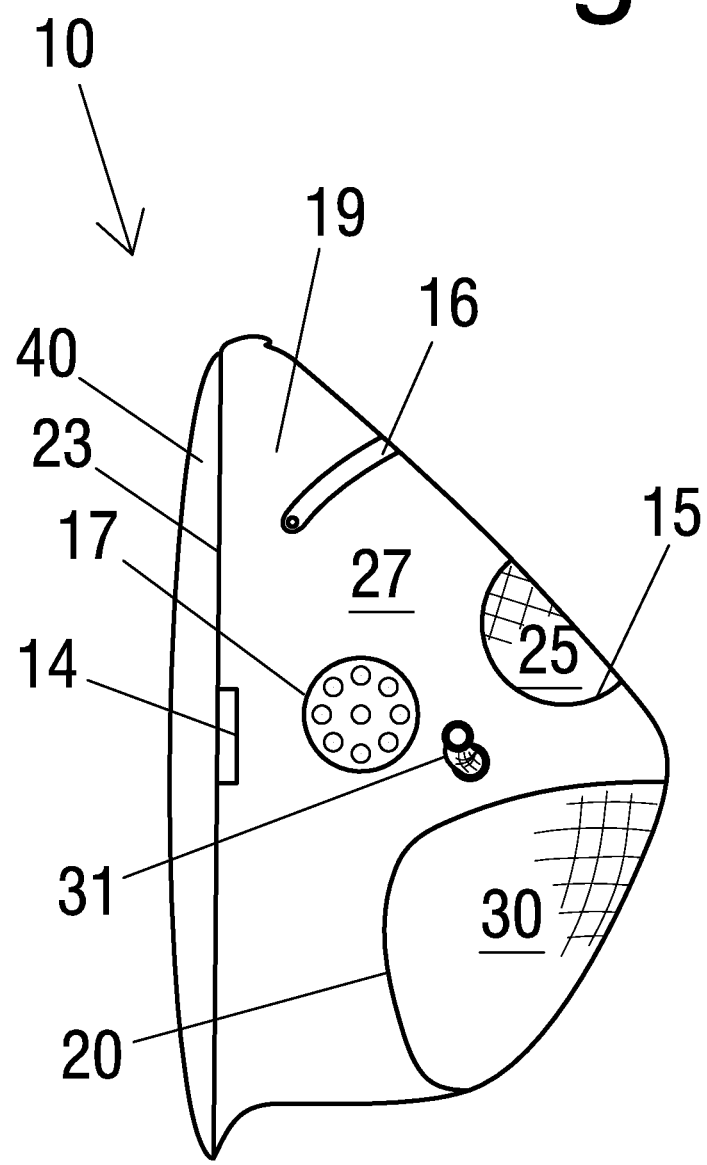

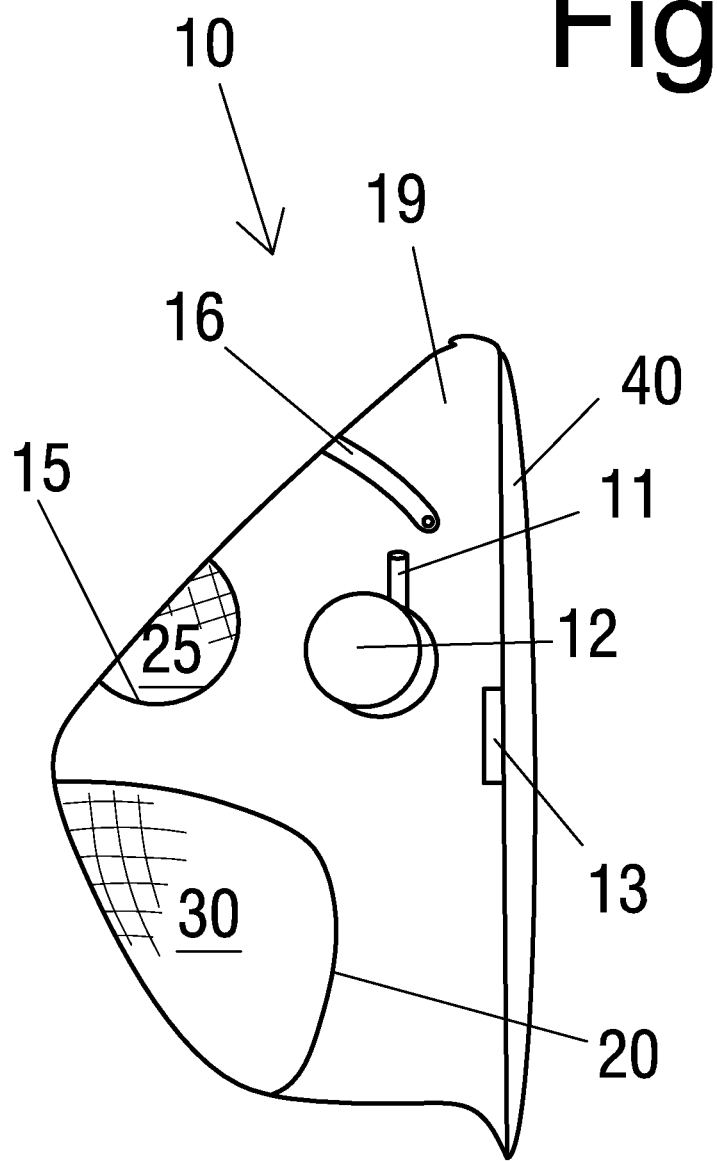

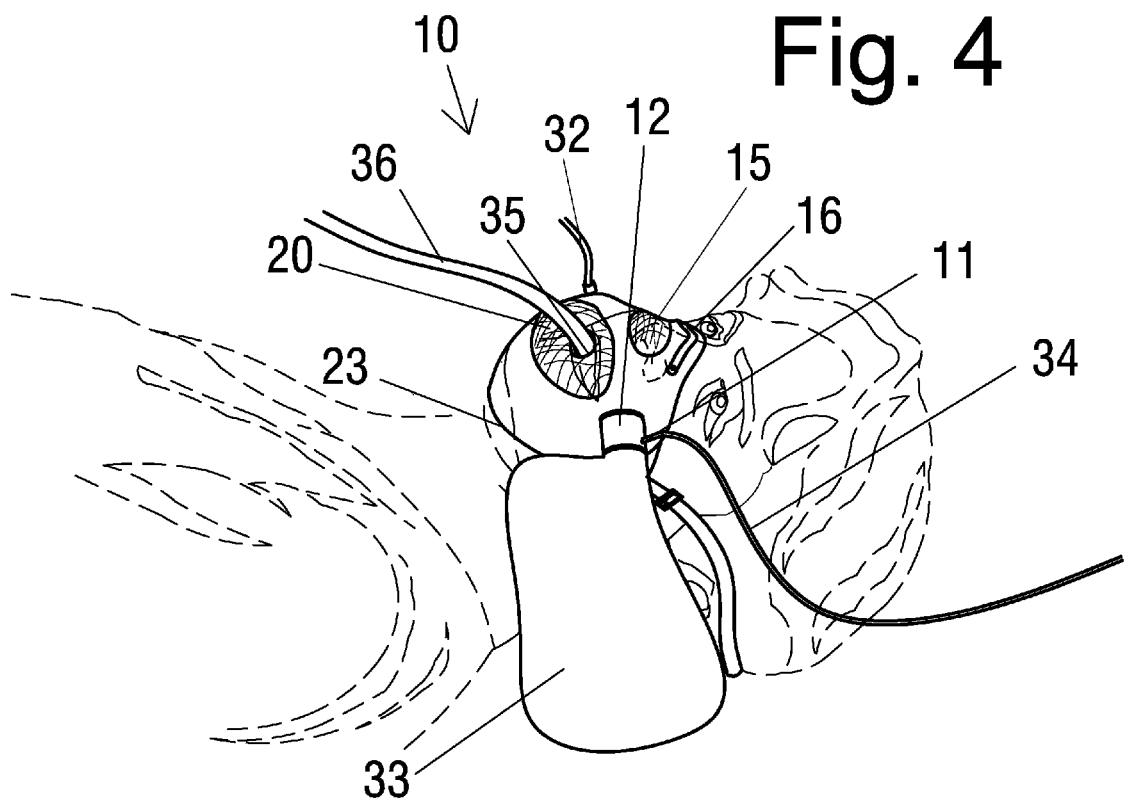

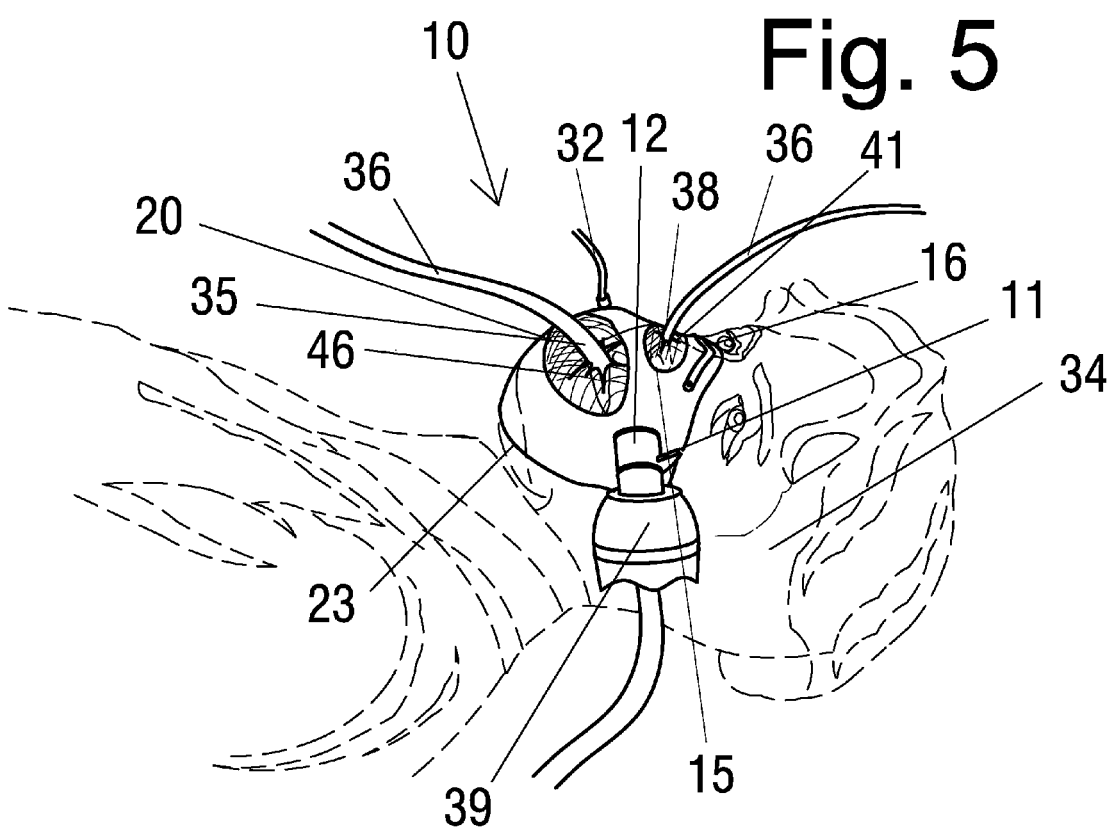

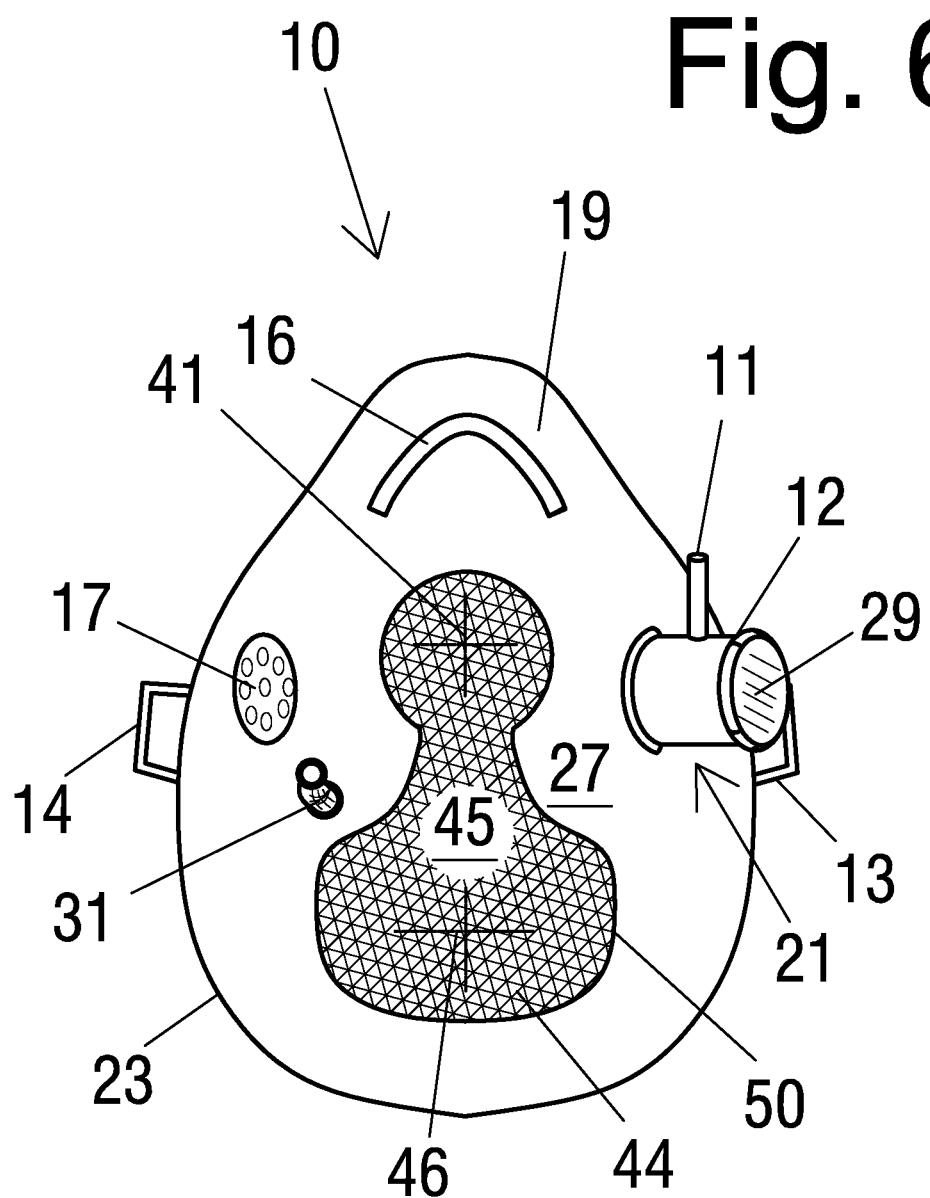

INTUBATION-FACILITATING OXYGEN MASK

CROSS-REFERENCE TO RELATED APPLICATION

This Continuation-in-Part application claims the benefit of U.S. patent application Ser. No. 12/764,31311/591,869, filed on Apr. 21, 2010, issued on Feb. 5, 2013 as U.S. Pat. No. 8,365,734, which claimed the benefit of Provisional Patent Application Ser. No. 61/173,816, filed on Apr. 29, 2009, which are incorporated herein in their entirety.

FIELD OF THE INVENTION

The present invention relates generally to a medical device, and more particularly, to an oxygen mask configured with at least one perforatable, modifiable membrane, which is beneficially positioned to allow nasal or oral procedures after manual configuration by an attending clinician at the time of the procedure.

DESCRIPTION OF THE PRIOR ART

Providing sufficient oxygen to a patient is vital. A nasal cannula can be used to provide supplemental oxygen, but at times it is necessary to use a standard oxygen mask (a face mask contoured to fit over a patient's nose and mouth) to deliver a higher concentration of breathable oxygen gas. For example, if a procedure is begun with nasal cannula, but then the patient begins to need more oxygen, switching to an oxygen mask at that time is difficult and does not provide optimum oxygen to the patient. Thus an oxygen mask that can be worn before and during procedures plus is designed to allow any of a wide variety of anticipated or unanticipated scope, probe, and tube orotracheal or nasotracheal procedures, would be highly advantageous.

Although, conventional intubation masks are available, they are not versatile. They are generally particularly designed for either oral entry or nasal entry and a specific type of scope, probe, or tube; therefore, if the situation changes, the chosen mask may not allow access to the necessary point of entry with the necessary medical device. By contrast, the intubation-facilitating oxygen mask of the present invention provides complete choice to the attending clinician.

Further, other treatments and monitoring may be required, such as breathing-therapy treatments and monitoring of expired gases to determine the condition of the patient. While conventional intubation masks do not provide for these, there is a need for additional versatility, allowing quick and easy connection of carbon dioxide monitors and of a variety of breathing-therapy devices such as might be required, for example, a non-rebreather bag, bubble humidifier, humidifier nebulizer, drug nebulizer, etc.

Accordingly, there is an established need for a highly versatile intubation-facilitating oxygen mask that allows the attending medical personnel to choose the correct point of entry, while optionally allowing monitoring of expired gases, allowing treatment by any of a variety of breathing-therapy devices, increasing patient safety and comfort, and greatly increasing inspired and expired oxygen percentages—thus insuring that the medical personnel can offer the widest range of options available for the safest treatment possible.

SUMMARY OF THE INVENTION

The present invention is directed to a versatile, intubation-facilitating oxygen mask that can be worn as an oxygen mask during standard oxygen therapy with the diaphragm or diaphragms in an unruptured, continuous state; and with the option, if need arises, to be quickly converted into an intubation mask by the rupturing of a diaphragm. This is done without disturbing the ongoing benefit to the patient of the increased oxygen saturation achieved by wearing the oxygen mask. Additionally, the oxygen mask of the present invention optionally enables the continuous monitoring of the expired gases through the carbon dioxide sampling port and the use of breathing-therapy devices.

The intubation-facilitating oxygen mask includes at least one novel modifiable diaphragm and a standard oxygen tube connector. Preferably the intubation-facilitating oxygen mask also includes a multiple-inlet port (comprising an interchangeable breathing-therapy device connector and preferably the standard oxygen tube connector), a carbon dioxide sampling port, an exhaust port, and a nose clip. Each of the one or more modifiable diaphragms is configured with a thin, continuous, flexible, perforatable, modifiable membrane from which an instrument-access port may be manually created or constructed, when and if needed. The interchangeable breathing-therapy device connector allows attachment of any breathing-therapy device, such as, for example, a non-rebreather bag or nebulizer.

The at least one novel modifiable diaphragm provides access to the nasal area and to the oral area of the patient. The at least one modifiable diaphragm may be configured as a single nasal/oral diaphragm with a single membrane extending over both the nose and mouth of the patient, or the modifiable diaphragm may be configured as two discrete membranes, forming a separate nasal diaphragm and separate oral diaphragm. Additionally, the modifiable diaphragm is preferably formed of a continuous membrane that is not smooth, but textured. The roughened or non-uniform texture allows the medical instrument to slide more easily against the diaphragm, reducing the adherence of the instrument to the diaphragm.

Because the continuous membrane of the modifiable diaphragm is manually perforated and altered by the clinician at the time of use, the point of entry and size of entry is completely under the control of the clinician, so can be perfectly matched to the requirements for any of the variety of procedures that may be performed involving any nasally or orally introduced medical instrument, such as a scope, probe, tube, or the like. These procedures include, for example, esophagogastroduodenoscope (EGD), bronchoscope, fiber-optic endoscopy, transesophageal echocardiography (TEE), and awake intubation. The material of the diaphragm provides a partial but significant seal around the scope or probe, retaining the oxygen therapy advantages (after the clinician perforates the diaphragm for the procedure to be performed and the tube is inserted).

As an aid to the clinician in the creation of a hole in the diaphragm for receiving the medical instrument, the membrane of the modifiable diaphragm preferably includes perforations that enable the clinician to easily rupture the diaphragm in the desired location without the use of a tool.

An object of the present invention is to provide an intubation-facilitating oxygen mask that can be adapted for use as an intubation mask for use with a wide variety of medical instruments, such as scopes, probes, and tubes.

A further object of the present invention is to provide an intubation-facilitating oxygen mask that is relatively inexpensive and disposable.

Another object of the present invention is to provide an intubation-facilitating oxygen mask that is configured to allow a clinician to quickly convert the intubation-facilitating oxygen mask from a standard oxygen mask to an endoscopic or intubation mask.

An additional object of the present invention is to provide for increased oxygen saturation.

A further object of the present invention is to provide an intubation-facilitating oxygen mask that can optionally be configured to allow continuous monitoring of carbon dioxide of expired gases.

Another object of the present invention is to provide convenient nasal or oral access for intubation, allowing the attending clinical to choose the correct point of entry and size of entry as needed to perform any of a variety of procedures.

An additional object of the present invention is to provide an intubation-facilitating oxygen mask that may optionally be configured to conveniently allow attachment of a non-rebreather bag to greatly increase inspired and expired oxygen percentages.

A further object of the present invention is to provide a high oxygen flow mask that does not need to be inflated and does not need to use positive pressure to function efficiently.

These and other objects, features, and advantages of the present invention will become more readily apparent from the attached drawings and from the detailed description of the preferred embodiments, which follow.

BRIEF DESCRIPTION OF THE DRAWINGS

The preferred embodiments of the invention will hereinafter be described in conjunction with the appended drawings, provided to illustrate and not to limit the invention, where like designations denote like elements, and in which:

FIG. 1 is a front view showing a first embodiment of the intubation-facilitating oxygen mask of the present invention;

FIG. 2 is a right side view showing the first embodiment of the intubation-facilitating oxygen mask of the present invention;

FIG. 3 is a left side view showing the first embodiment of the intubation-facilitating oxygen mask of the present invention;

FIG. 4 is a perspective view showing the first embodiment of the intubation-facilitating oxygen mask of the present invention in use;

FIG. 5 is a perspective view showing the first embodiment of the intubation-facilitating oxygen mask of the present invention in a second use; and FIG. 6 is a front view showing a preferred second embodiment of the intubation-facilitating oxygen mask of the present invention.

Like reference numerals refer to like parts throughout the several views of the drawings.

DETAILED DESCRIPTION OF THE PREFERRED EMBODIMENTS

Shown throughout the figures, the present invention is directed toward a versatile, intubation-facilitating oxygen mask having at least one diaphragm sealed with a continuous membrane. The intubation-facilitating oxygen mask is usable as a standard oxygen mask, but, if the need arises, it is quickly and easily convertible to an intubation mask by manual creation of an instrument-access port by perforating and adapting the continuous modifiable membrane of the diaphragm to fit the medical instrument to be used in the particular medical procedure. For example, medical instruments such as scopes, probes, and tubes used for the following procedures are conveniently accommodated: esophagogastroduodenoscopy (EGD), awake intubation, fiber-optic endoscopy, transesophageal echocardiography (TEE), bronchoscopy, and other orotracheal or nasotracheal intubations. The novel intubation-facilitating oxygen mask is designed to provide an increase in a patient's oxygen saturation before and during intubation. Further, the available optional multiple ports offer convenient optional connections for other medical devices that may be needed.

Two embodiments are presented herein. The first embodiment has an oral diaphragm and a separate nasal diaphragm (FIGS. 1-5), and the second embodiment has a single oral/nasal diaphragm (FIG. 6). Two additional aspects are herein disclosed, either or both of which may be used with the first or the second embodiment. In one aspect of the invention, the diaphragm or diaphragms may be configured with tearing-facilitating sections providing convenient modification of the diaphragm, as shown in FIGS. 1, 5, 6. In a second aspect of the invention, the membrane of the diaphragm or diaphragms may be textured to reduce friction between the diaphragm and the medical instrument being used.

Referring now to FIG. 1, the intubation-facilitating oxygen mask, shown generally as reference number 10, is illustrated in accordance with a first embodiment of the present invention. As shown, the intubation-facilitating oxygen mask comprises the following elements: a mask body 19, a nasal diaphragm 15 (with continuous nasal modifiable membrane 25); and an oral diaphragm 20 (with continuous oral modifiable membrane 30); a multiple-inlet port 21 configured with two connectors (a standard oxygen tube connector 11 and an interchangeable breathing-therapy device connector 12); a carbon dioxide sampling port 31; an exhaust port 17; a nose clip 16; and two strap attachments 13, 14. The novel mask is preferably lightweight, comfortable to wear, ergonomically shaped, and disposable.

The generally concave mask body 19 is preferably molded of a generally gas-impermeable material, such as non-toxic medical grade plastic polymer material (i.e., silicone, polyester, or, preferably, polyvinyl chloride [PVC]). The mask material is preferably partially or substantially transparent to allow clinicians to observe the patient's condition. The mask body 19, connections and attachments are preferably disposable. The two strap attachments 13, 14 are configured to receive a conventional adjustable elastic retaining strap to secure the mask body to the patient's head. The two strap attachments 13, 14 are disposed on opposing sides of the mask body 19 and are preferably integrally molded with mask body 19.

The mask body 19 has a peripheral edge 23, a nasal aperture (nasal diaphragm 15 occluded or sealed by nasal modifiable membrane 25), an oral aperture (oral diaphragm 20 occluded or sealed by oral modifiable membrane 30), an outer surface 27, and an inner surface 40 (the inwardly facing surface generally opposing outer surface 27, which defines a cavity adapted to fit over the mouth and at least the lower region of the nose of a patient). The surrounding peripheral edge 23 is preferably contoured so as to substantially seal against the surrounding facial tissue of the patient, to thereby establish an interior chamber portion. The mask body 19 has a nasal zone and an oral zone, in the general areas of the nose and mouth of the patient when the mask is placed in position on the patient's face. The peripheral edge 23 may, optionally, have an enhanced seal, such as, for example, an air cushion or foam.

The mask body 19 preferably has an adjustable nose clip 16 disposed in the upper nasal zone, which can be adjusted to conform to the nose to stabilize the intubation-facilitating oxygen mask in position on the patient's face.

A carbon dioxide sampling port 31 is optionally, but preferably disposed in a generally central area of the mask body 19. This positioning near the nostrils of the patient allows accurate sampling of the expired gases breathed into the cavity formed by the mask body 19.

The intubation-facilitating oxygen mask 10 also preferably includes a multiple-inlet port 21. The multiple-inlet port preferably comprises both a standard oxygen tube connector 11 and an interchangeable breathing-therapy device connector 12.

The standard oxygen tube connector 11 is configured to accept a standard oxygen tube 34 (FIG. 4), allowing the breathable oxygen gas from a storage tank to flow to the patient through the connector 11. Conventionally, the oxygen tubing 34 has a proximal end fitted with a funnel shape connector for easy connection to the standard oxygen tube connector 11. The standard oxygen tube connector 11 is, optionally, a fixed connector or a swivel connector. The intubation-facilitating oxygen mask 10 can be used with up to approximately 15 liters of oxygen per minute.

The interchangeable breathing-therapy device connector 12 is configured to allow attachment of one of a number of conventional breathing-therapy devices, as required in the particular medical situation. Also, a first breathing-therapy device 33 (FIG. 4) may be attached to connector 12 for a first period of time, then removed, and a second breathing-therapy device may then be attached. The breathing-therapy device 33 that can be connected to connector 12 include, for example, a non-rebreather bag 37, bubble humidifier, humidifier, or drug nebulizer 39, etc. Use of the non-rebreather bag with the novel oxygen mask, increases inspired and expired oxygen percentages by 300% for the patient with respiratory issues.

A cap 29 is preferably initially installed on the interchangeable breathing-therapy device connector 12, which is removable for usage of the connector 12.

One or more exhaust ports 17 are disposed in a generally central area of the mask body 19, allowing expired gases to be discharged. The exhaust port(s) 17 may include a one-way valve or may include perforations allowing free flowing of the expired gases. The exhaust port(s) 17 may be formed integrally with the molded mask body 19 or may be non-removably inserted into the mask body 19.

The nasal diaphragm 15 and oral diaphragm 20 are both configured with a thin, continuous, flexible, perforatable, modifiable membrane 25, 30. The modifiable membrane 25, 30 extends across and completely seals the diaphragm 15, 20. The modifiable membrane is formed of a thin, flexible material, such as a plastic polymer material, and is preferably formed of polyvinylchloride. Other polymer materials, such as polyethylene, polyester, polyimide, polyolefin, polypropylene, polyvinylchloride, or the like may optionally be used. The diaphragm material provides a partial but significant seal around the scope or probe, allowing increased oxygen saturation for the patient. Optionally, the polymer material may have a degree of elasticity that allows the membrane 25, 30 to enfold the tube, scope, or probe, after being manually perforated to fit the particular tube or probe to be used.

The modifiable membrane may be formed integrally and unitarily with the mask body or may be formed separately and permanently joined to the mask body. The modifiable membrane may be thinner than the other areas of the mask body, for example, 20-40% thinner.

Preferably, as shown in FIG. 1, the modifiable membranes 25, 30 are configured with tearing-facilitating sections 41, 46 to allow the attending clinician to manually create a hole in the needed area without using an implement or tool to do so. The tearing-facilitating sections 41, 46 aid in tearing along a predetermined line. The tearing-facilitating sections 41, 46 may be perforations, scoring, notches, furrows or the like which allow convenient opening along the predetermined line or lines of the diaphragm 15, 20. However, modifiable membranes 25, 30 without tearing-facilitating sections 41, 46 are also within the scope of the invention, as shown in FIGS. 2-4.

Also, as shown in FIG. 1, the modifiable membranes 25, 30 of the diaphragms 15, 20 are preferably textured with a texture 44. Texture 44 may be only on the top surface of the membranes or may be on both the top and bottom surfaces. Texture 44 may be a roughness, graininess, or a regular or irregular pattern, but is preferably an integrated, rough textured surface. The texture 44 serves to reduce friction between the diaphragm and the medical instrument 36 being used so the instrument is not retarded or slowed during use. The texture 44 permits the tube or scope to slide smoothly without holding or adhering to the modifiable membranes 25, 30. However, a smooth, non-textured membrane 25, 30 is also within the scope of the invention.

The nasal diaphragm 15, disposed in the nasal zone of mask body 19, is positioned to accommodate nasotracheal intubations; the oral diaphragm 20, disposed in the oral zone of mask body 19, is positioned to accommodate orotracheal intubations. As the membrane 25, 30 of either the nasal 15 or oral diaphragm 20 is manually perforated and modified by the clinician at the time of use, the point of entry and size of entry is completely under the control of the clinician, so can be perfectly matched to the requirements for any of the variety of procedures that may be performed.

The second embodiment of the oxygen mask is shown in FIG. 6, which embodies many of the features of the first embodiment, but discloses a single oral/nasal diaphragm 50 in which a single membrane 45 extends over both the oral area and the nasal area; the oral/nasal diaphragm 50 provides access to both the area of the nasal diaphragm 15 and the area of the oral diaphragm 20 of the first embodiment. The diaphragm is sized large enough, is shaped, and is configured to give access to both areas. The shape may be generally rectangular, may be oval-shaped, may have a narrowed waist (as illustrated in FIG. 6), may be two circular shapes joined by an isthmus, or may be any other shape that gives access to both the oral and nasal cavities. A single continuous modifiable membrane 45 extends across and completely seals the oral/nasal diaphragm 50.

Either of the two aspects (texture 44 and tearing-facilitating sections 41, 46) of the invention described above may be used with the single oral/nasal diaphragm 50 of the second embodiment. As shown in FIG. 6, the tearing-facilitating sections 41, 46 are disposed in the proper location to give access to the nose and mouth of the patient. Though an exemplary patterned texture 44 is shown in FIG. 6, any uniform or non-uniform pattern or texture may be used to provide the advantages of a less-adherent surface.

To use the novel intubation-facilitating oxygen mask 10, the novel mask 10 is positioned on a patient's face covering the mouth and at least a portion of the nose with the inner surface 40 toward the patient's face. The nose clip 16 is modified to fit the patient's nose and the elastic retaining strap (connected to the mask 10 at strap attachments 13, 14) is used to secure the mask body 19 to the patient's head. The novel mask 10 can be used as a standard oxygen mask and worn routinely during oxygen therapy, and then, without interruption, used for an unanticipated intubation; or it can be placed on the patient in anticipation of an intubation.

First an oxygen tube is connected to the oxygen tube connector 11 of multiple-inlet port 21, delivering oxygen to the patient. If intubation is needed, the attending clinician determines the procedure to be performed and notes the tube, scope, or probe to be used. The clinician then perforates the modifiable membrane(s) 25, 30 of the appropriate diaphragm(s) (nasal diaphragm 15 and/or oral diaphragm 20, or the nasal area of oral/nasal diaphragm 50 and/or the oral area of oral/nasal diaphragm 50) to create an instrument access point 35, 38 (FIG. 5). If the preferred tearing-facilitating sections 41, 46 are provided, the clinician perforates the modifiable membrane(s) 25, 30 along the predetermined line or lines. The instrument 36 is then advanced into the oral orifice or nasal orifice of the patient (in correspondence to the procedure to be performed.) The texture 44 allows the instrument 36 to advance smoothly, without a tendency to adhere to the membrane. If desired, a tube 32 from a carbon dioxide monitor (such as a capnograph) is attached to the carbon dioxide sampling port 31. Further, if needed, cap 29 is removed and a breathing-therapy device 33 is attached to the interchangeable breathing-therapy device connector 12.

The intubation procedure then proceeds, with the intubation-facilitating oxygen mask 10 providing oxygen to the patient, allowing continual monitoring of expired gases, and allowing use of a breathing-therapy device 33 (FIG. 4), such as a non-rebreather bag, thereby greatly increasing the inspired and expired oxygen percentages.

From the foregoing, it will be apparent that the intubation-facilitating oxygen mask 10 of the current invention provides an inexpensive, disposable novel mask 10 that provides a standard oxygen mask that also allows convenient nasal or oral access while providing high oxygen flow, without using positive pressure or inflation. The novel mask is well-suited for use with a wide variety of medical scopes, probes, and tubes. The unique modifiable membrane of the at least one diaphragm allows a clinician to quickly convert the intubation-facilitating oxygen mask from a standard oxygen mask to an endoscopic mask.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

I claim:

1. A face mask for delivering breathable gas to a patient, comprising:
    a concave mask body having a peripheral edge, an outer surface, and an inner surface defining a cavity, adapted to fit over the mouth and at least the lower region of the nose of the patient;
    at least one diaphragm, wherein each one of said at least one diaphragm is sealed by a continuous, perforatable, modifiable membrane from which an instrument-access port can be manually constructed, wherein said modifiable membrane is configured with a first tearing-facilitating section adapted to be arranged over the mouth and a separate second tearing-facilitating section adapted to be arranged over a lower region of the nose of the patient; and a standard oxygen tube connector configured to allow a tube delivering breathable gas to be attached.

2. The face mask for delivering breathable gas to a patient, as recited in claim 1, further comprising a carbon dioxide sampling port configured to allow monitoring of expired gasses.

3. The face mask for delivering breathable gas to a patient, as recited in claim 1, further comprising an exhaust port.

4. The face mask for delivering breathable gas to a patient, as recited in claim 1, further comprising a nose clip to assist in retaining said face mask on a face.

5. The face mask for delivering breathable gas to a patient, as recited in claim 1, wherein said face mask is disposable.

6. The face mask for delivering breathable gas to a patient, as recited in claim 1, further comprising a multiple-inlet port configured with an interchangeable breathing-therapy device connector adapted to allow fluid communication between a breathing-therapy device and said cavity formed by said inner surface.

7. The face mask for delivering breathable gas to a patient, as recited in claim 6, wherein said standard oxygen tube connector is disposed on said multiple-inlet port.

8. The face mask for delivering breathable gas to a patient, as recited in claim 6, wherein said breathing-therapy device comprises a non-rebreather bag.

9. The face mask for delivering breathable gas to a patient, as recited in claim 1 wherein the first tearing-facilitating section and second tearing-facilitating section comprise perforations.

10. The face mask for delivering breathable gas to a patient, as recited in claim 1, wherein said face mask includes only one diaphragm, sealed by a continuous, perforatable, modifiable membrane from which an instrument-access port can be manually constructed, wherein said only one diaphragm is adapted to be arranged over the mouth and a lower region of the nose of the patient.

11. The face mask for delivering breathable gas to a patient, as recited in claim 10, wherein said modifiable membrane is configured with a tearing-facilitating section adapted to be arranged over the mouth and a separate tearing-facilitating section adapted to be arranged over a lower region of the nose of the patient.

12. A method for providing a breathable gas to a patient, comprising the steps of:
    providing a face mask configured with a standard oxygen tube connector and at least one diaphragm sealed by a continuous, perforatable, modifiable membrane from which an instrument-access port can be manually constructed, wherein said modifiable membrane is configured with a first tearing-facilitating section adapted to be arranged over the mouth and a separate second tearing-facilitating section adapted to be arranged over a lower region of the nose of the patient; placing said face mask over the face of said patient;
    attaching a tube delivering breathable gas to said standard oxygen tube connector;
    supplying breathable gas to said patient;
    perforating said modifiable membrane to create an instrument-access port, with the perforation location based on an intubation procedure to be performed;
    inserting an instrument associated with said intubation procedure through said instrument-access port; and
    advancing said instrument into either the oral orifice or nasal orifice of said patient while supplying said breathable gas to said patient.

13. The method for providing a breathable gas to a patient, as recited in claim 12, wherein said face mask is further configured with a carbon dioxide sampling port and further comprising attaching a tube from a carbon dioxide monitor to said carbon dioxide sampling port.

14. The method for providing a breathable gas to a patient, as recited in claim 13, wherein said face mask is further configured with an interchangeable breathing-therapy device connector and further comprising attaching a breathing-therapy device to said interchangeable breathing-therapy device connector.

15. The method for providing a breathable gas to a patient, as recited in claim 14, wherein said breathing-therapy device comprises a nebulizer.

16. The method for providing a breathable gas to a patient, as recited in claim 14, wherein said breathing-therapy device comprises a non-rebreather bag.

17. The method for providing a breathable gas to a patient, as recited in claim 12 wherein the first tearing-facilitating section and second tearing-facilitating section comprise perforations.

18. A method for providing a breathable gas to a patient, comprising the steps of:
    providing a face mask configured with a standard oxygen tube connector and a diaphragm sealed by a continuous, perforatable, modifiable membrane from which an instrument-access port can be manually constructed, wherein said diaphragm is adapted to be arranged over the mouth and a lower region of the nose of the patient, and wherein said modifiable membrane is configured with a first tearing-facilitating section adapted to be arranged over the mouth and a separate second tearing-facilitating section adapted to be arranged over a lower region of the nose of the patient;
    placing said face mask over the face of said patient;
    attaching a tube delivering breathable gas to said standard oxygen tube connector;
    supplying breathable gas to said patient;
    perforating said membrane at said first tearing-facilitating section and/or said second tearing-facilitating section to create an instrument-access port arranged over the mouth and/or the lower region of the nose of the patient, with the perforation location based on an intubation procedure to be performed;
    inserting an instrument associated with said intubation procedure through said instrument-access port; and
    advancing said instrument into either the oral orifice or nasal orifice of said patient while supplying said breathable gas to said patient.

* * * * *